United States Patent [19]

Archibald et al.

[11] 3,933,829

[45] Jan. 20, 1976

[54] 4-AMINOQUINOLINE DERIVATIVES

[75] Inventors: John Leheup Archibald, Windsor; John Terence Arnott Boyle; John Christopher Saunders, both of Maidenhead, all of England

[73] Assignee: John Wyeth & Brother Limited, Maidenhead, England

[22] Filed: Aug. 22, 1974

[21] Appl. No.: 499,746

[52] U.S. Cl.... 260/288 R; 260/283 A; 260/283 SA; 260/287 AR; 260/288 CE; 260/298.85; 260/326.82; 260/556 B; 424/258
[51] Int. Cl.² .................................... C07D 215/44
[58] Field of Search.... 260/283 SA, 288 R, 288 CE, 260/287 AR

[56] References Cited
UNITED STATES PATENTS

| | | | |
|---|---|---|---|
| 3,150,047 | 9/1964 | Allais et al. | 260/287 AR |
| 3,769,410 | 10/1973 | Bertrand | 260/287 AR |
| 3,819,633 | 6/1974 | Ambrogi et al. | 260/283 SA |

*Primary Examiner*—Donald G. Daus
*Assistant Examiner*—Mary C. Vaughn

[57] ABSTRACT

The disclosure describes new 4-aminoquinoline derivatives of general formula

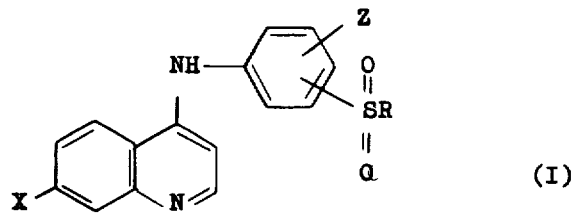

and their acid addition salts, where X is a halogen atom or a trifluoromethyl group, Z is a hydrogen atom or a defined substituent, R is group of the formula

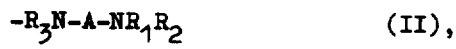 (II),

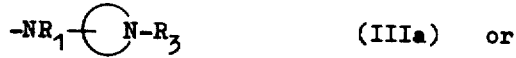 (IIIa) or

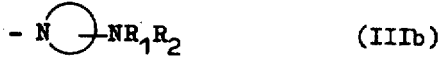 (IIIb)

where A in formula II is a chain of 1 to 5 methylene groups which may be substituted with alkyl, the ring in formula IIIa and IIIb is a piperidine or pyrrolidine ring that may be substituted with alkyl and $R_1$, $R_2$ and $R_3$ represent hydrogen or certain defined substituents. The new 4-aminoquinoline derivatives show antihypertensive activity and, in some cases, show one or more of the following activities: anti-malarial activity, anti-inflammatory activity, anti-trichomonal activity and inhibition of blood platelet aggregation.

9 Claims, No Drawings

4-AMINOQUINOLINE DERIVATIVES

The present invention concerns new 4-aminoquinoline derivatives, a process for their preparation and pharmaceutical compositions containing them. The invention also concerns new intermediates useful for the preparation of the 4-aminoquinoline derivatives.

The invention provides new 4-aminoquinoline derivatives of the general formula

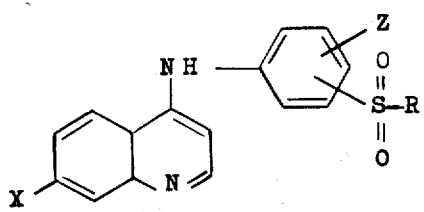

(I)

and their acid addition salts, where i. X is a halogen atom or a trifluoromethyl group;
ii. Z is a hydrogen atom or a halogen atom, a trifluoromethyl group, a lower alkyl group, a lower alkoxy group, a hydroxyl group, a nitro group, an amino group or a mono- or di-alkyl substituted amino group, and
iii. R represents a group of the formula $-NR_3-A-NR_1R_2$ (II) or

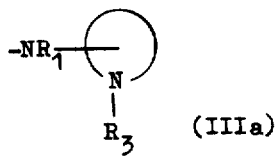 or 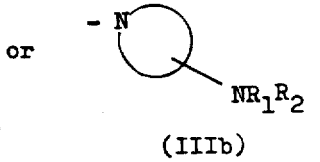

(IIIa)    (IIIb)

wherein:

a. in formula II, A represents a chain of 1 to 5 methylene groups, which may be substituted by one or more alkyl groups;
b. in formula IIIa and IIIb the ring denotes a piperidine or pyrrolidine ring that may be substituted by one or more alkyl groups or by a divalent aliphatic chain substituting two different ring members of the piperidine or pyrrolidine ring;
c. $R_1$ represents a hydrogen atom, an alkyl group, an aralkyl group, an acyl group or an aryl group or, in formula II or IIIb, $R_1$ and $R_2$ may together form the diacyl residue of a dicarboxylic acid or $R_1$ and $R_2$ may together form a divalent radical such that $R_1R_2NH$ is a secondary cyclic amine with 5 to 7 ring atoms;
d. $R_2$ is as defined above in connection with $R_1$ or represents a hydrogen atom, an alkyl group, an aralkyl group or an acyl group; and
e. $R_3$ represents a hydrogen atom, a cycloalkyl group of 5 to 7 carbon atoms, an alkyl group, an aralkyl group, or an alkyl group substituted by a heterocyclic group, or an aliphatic chain joining the nitrogen atom member to another ring member of the ring in formula IIIa.

The invention also provides a new class of compounds useful as intermediates for the preparation of compounds of formula I and their acid addition salts. These new compounds are benzenesulphonamides having the formula

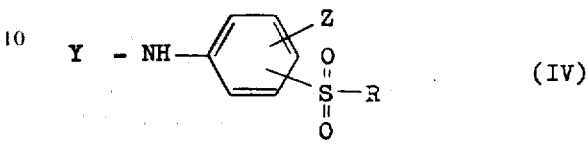

(IV)

and their acid addition salts, where R is as defined in connection with formula I, Z is as defined in connection with formula I or is a protected amino or hydroxyl group and Y is a hydrogen atom or a lower alkanoyl group.

It will be apparent to those skilled in the art that the above definition of R includes moieties possessing an asymmetric carbon atom, especially for instance, in the cases where 1. A is linear chain of 1 to 15 methylene groups, the chain being monosubstituted by methyl or ethyl, or
2. R is of the formula V or VI

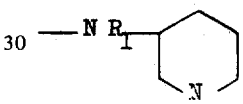

or (V)

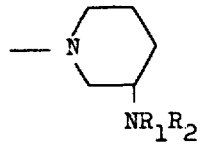

(VI)

for example, in the cases where R denotes groups of the formula

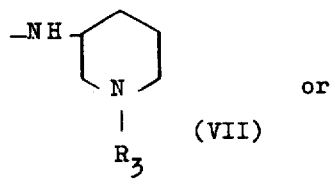

or (VII)

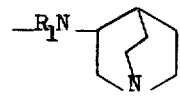

(VIII)

where $R_1$, $R_2$ and $R_3$ may be, for instance, hydrogen or lower alkyl. It is to be understood that general formulae I and IV are intended to encompass both enantiomers where the compound contains an asymmetric carbon atom and mixtures of the enantiomers, for instance, a racemic mixture of the enantiomers. General methods are recorded in the literature for the resolution of enantiomers.

In the compounds of formula I, X preferably represents a halogen atom, for example, a chlorine or bromine atom, but may also represent a trifluoromethyl group. Illustrative meanings of Z in formulae I and IV include hydrogen, chlorine, bromine atoms and trifluoromethyl, lower alkyl or alkoxy (for example, methyl, ethyl, propyl, butyl, methoxy, ethoxy, propoxy and butoxy), hydroxyl, nitro, amino, methylamino, ethylamino, dimethylamino and diethylamino groups. Additionally in formula IV, Z may be protected amino or protected hydroxyl group, for example a group of the formula IX

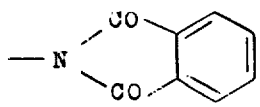

(IX)

In formulae II and IIIb $R_1$ and $R_2$ may be separate or may be joined together to form a divalent residue. The divalent residue is a diacyl residue of a dicarboxylic acid, for example, a group of the formula $-CO-(CH_2-)_n-CO-$ where $n$ is 2 or 3, or

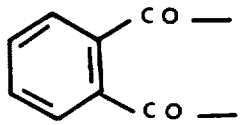

(X)

or is such that $R_1R_2NH$ is a secondary cyclic amine with 5 to 7 ring atoms, for instance, piperidine, pyrrolidine or morpholine.

ethyl, n- or i-propyl and n-butyl. Aryl groups particularly comprehend phenyl or phenyl substituted by one or more substituents. As substituents for a phenyl group there may be employed lower alkyl (for example, methyl, ethyl, propyl or butyl), lower alkoxy (for example, methoxy, ethoxy, propoxy or butoxy), nitro, halogen, (preferably chlorine or bromine), hydroxy, trifluoromethyl or amino (including mono- or dialkylamino, for instance, dimethylamino). Aralkyl groups are aryl-substituted alkyl groups, where the alkyl group is desirably a lower alkyl group (e.g. methyl, ethyl, propyl or butyl) and its aryl substituent may be phenyl or substituted phenyl, in which the one or more substituents for phenyl are as mentioned above.

Acyl groups particularly include the acyl groups of the formula $-CO.R_5$ where $R_5$ represents alkyl or aryl. As specific acyl groups there may be mentioned, for example, acetyl, propionyl, butanoyl, hexanoyl, benzoyl and benzoyl substituted by one or more of the above mentioned substituents for phenyl. As cycloalkyl of 5 to 7 carbon atoms there may be mentioned cyclopentyl, cyclohexyl and cycloheptyl. As alkyl substituted by a heterocyclyl group there may be mentioned lower alkyl such as methyl, ethyl, propyl or butyl, substituted by thienyl (for instance 2-thienyl), furyl, pyrrolyl, imidazolyl, pyrazolyl (for instance 4-pyrazolyl), indolyl, pyridyl (for instance 2- or 4-pyridyl), quinolyl, thiazolyl (specifically 2-, 4- or 5-thiazolyl), isothiazolyl or oxazolyl.

As examples of A in formula II there may be mentioned methylene, dimethylene, trimethyleme, tetramethylene and pentamethylene and their mono- or di-(lower alkyl) substitution products, for example, groups of the formulae

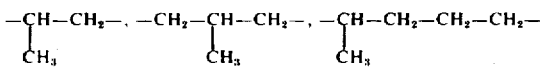

The piperidine of pyrrolidine ring shown in formulae IIIa and IIIb may be substituted with one or more alkyl groups, preferably lower alkyl groups, for example, methyl, ethyl, propyl or butyl. As examples of R containing a piperidine or pyrrolidine ring there may be mentioned groups of the formula:

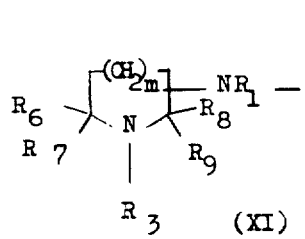 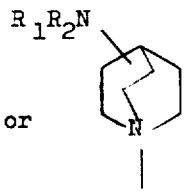 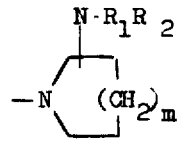

(XI)　　　　　(XII)　　　　　(XIII)

$R_1$, when in formula IIIa or when separate from $R_2$ in formula II or IIIb, represents a hydrogen atom, an alkyl group, an aralkyl group, an acyl group or an aryl group, $R_2$, when separate from $R_1$ in formulae II and IIIb, represents a hydrogen atom, an alkyl group, an aralkyl group or an acyl group. $R_3$ in formulae II and IIIa represents a hydrogen atom, a cycloalkyl group of 5 to 7 carbon atoms, an alkyl group, an aralkyl group, or an aliphatic chain joining the nitrogen ring atom to another ring atom of the ring shown in formula IIIa. Illustrative examples of such groups that can be denoted by $R_1$, $R_2$ or $R_3$ will now be described. Alkyl groups are desirably lower alkyl groups, for example, methyl, where $m$ is 0 or 1; $R_1$, $R_2$ and $R_3$ are as defined above; and $R_6$, $R_7$, $R_8$ and $R_9$, which may be the same or different may be hydrogen or lower alkyl, for instance, methyl, ethyl, propyl or butyl.

In formula IV the symbol Y denotes a hydrogen atom or a lower alkanoyl group, for example, acetyl, propionyl, butanoyl or hexanoyl.

In formulae I and IV the $-SO_3R$ group is preferably at the para-position relative to the 7-substituted-4-quinolylamino group in formula I and the group Y—NH— in the case of formula IV. Thus the preferred new compounds of the invention are those of the formulae Ia and IVa

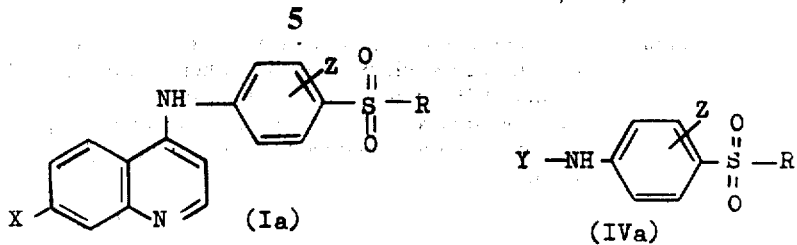

The term "lower" as used herein in connection with such groups as "alkanoyl", "alkyl" or "alkoxy" denotes that the group contains up to 6 carbon atoms, preferably up to 4 carbon atoms.

Examples of acid addition salts are those formed from inorganic and organic acids and in particular include sulphate, hydrochloride, hydrobromide, hydroiodide, nitrate, phosphate, sulphonate (such as the methanesulphonate and p-toluene-sulphonate), acetate, maleate, fumarate, tartrate, malonate, citrate and formate.

The compounds of the formula I may be made by building the compound up by known reactions. In particular the sulphonamide linkage shown in formula I may be formed by sulphonylation of an appropriate amine, and an amino-benzene sulphonamide may be converted to the secondary amine by introducing the 7-(halo or trifluoromethyl)-4-quinolyl group in known manner.

The invention provides a method of making compounds of the formula I and their acid addition salts, wherein a compound of the formula RH, where R is as defined in connection with formula I, or, where necessary or desired, a corresponding compound with a protecting group, is sulphonylated to introduce the sulphonyl group of formula XIV

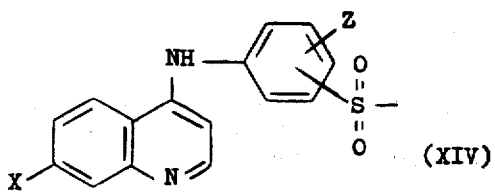

where X is defined in connection with formula I and Z is as defined in connection with formula IV.

As sulphonating agent there may particularly be used a sulphonyl chloride of formula XV

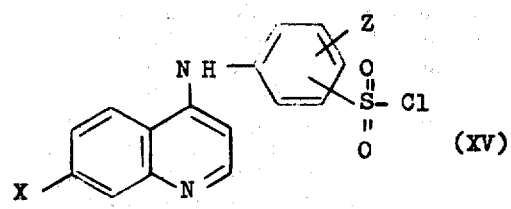

where X is as defined above and Z is as defined in connection with formula IV. Alternatively, a compound of the formula XVI

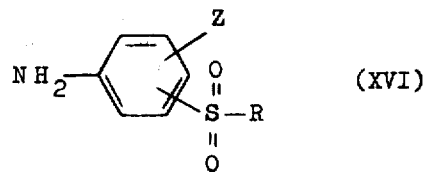

(where R and Z are as defined in connection with formula IV is reacted with a compound of formula (XVII)

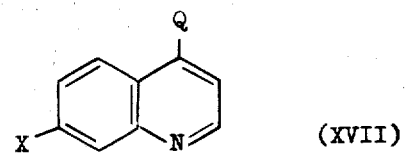

(where X is as defined above in connection with formula I and Q denotes a group or atom replaceable by nucleophilic attack by compound of formula XVI). Q is for example, an iodine atom, a bromine atom or a chloride atom or an organosulphonate group, for instance, p-toluenesulphonate.

Where necessary or if desired, the process may also include removal of a protecting group, and if desired, conversion of a free base form of compound of formula I into an acid addition salt or conversion of an acid addition salt form of a compound of formula I into the corresponding free base form.

Starting materials of formula RH and formulae XV are known compounds or, if new, are accessible by conventional methods.

The sulphonylation method may be carried out by reacting the compound of formula XV with the compound of formula RH or a corresponding compound with a protecting group in chloroform in the presence of a saturated sodium carbonate solution.

It will be apparent to those skilled in the art that certain unacylated compounds of formula RH may present more than one potentially reactive location for sulphonylation. Undesired sulphonylation may be avoided by chemical protection with removable blocking groups or other means. For example, the compounds of the formula

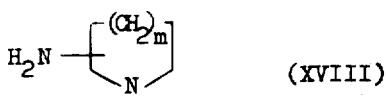    (XVIII)

(wherein n is 0 or 1) may be sulphonylated at the ring nitrogen atom by using a starting material in which the NH₂ function is protected with a blocking group which is removed after acylation.

Compounds of formula I and their acid addition salts, in which, in formula IIIa, R₃ denotes hydrogen, may be prepared by using, for example, a benzyl group as removable protecting group. Thus a starting compound of formula:

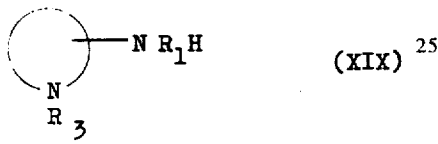    (XIX)

in which R₃ is benzyl is sulphonylated and the protecting group is removed after sulphonylation by debenzylation. Debenzylation may be carried out using sodium in liquid ammonia or by catalytic hydrogenation under conditions such that the 7-halo- or 7-trifluoromethyl substituents on the quinolyl group is not removed. In addition, compounds of formula RH include compounds where a substituent on an aryl group or heterocyclyl group is susceptible to sulphonylation, e.g. a free hydroxyl or amino substituent. Such substituents may be protected with a removable blocking group which is cleaved off after sulphonylation. Sulphonylating derivatives for introducing the group of formula XIV include protection for a group Z sensitive to sulphonylation. For example, a final product in which Z is an amino function can be formed by using a sulphonylating derivative of the acid formula XX.

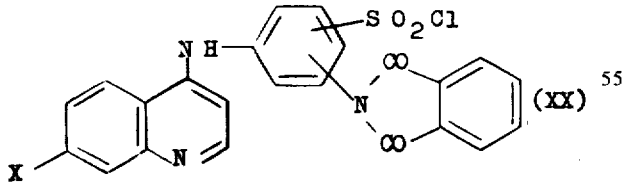    (XX)

and, after sulphonylation, converting the phthalimido group to an NH₂ group by reaction with hydrazine. The new compounds of the invention are comparatively stable to hydrolysis and therefore favour protecting groups that are readily hydrolysed off under acid or basic conditions.

Compounds of the formula IV and their acid addition salts are accessible by a process wherein a compound formula RH where R is as defined in formula I, or a corresponding compound with a protecting group, is sulphonylated to introduce the sulphonyl group of formula:

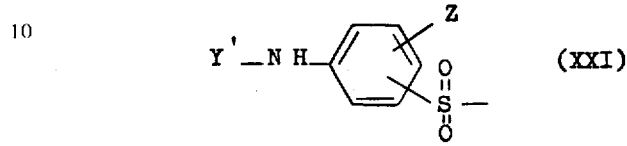    (XXI)

where Y' is a lower alkanoyl group and Z is as defined above in connection with formula IV. The sulphonylating agent used is preferably the sulphonyl chloride of formula:

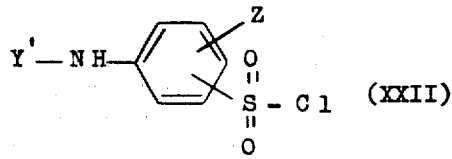    (XXII)

where Y' and Z are as defined in formula XXI. The corresponding sulphonylation product has the formula:

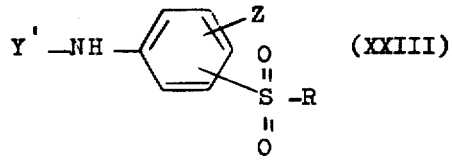    (XXIII)

This product may be isolated as such or as an acid addition salt. This product may then be converted to the compound of formula XVI

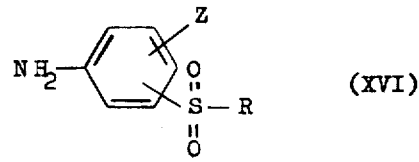    (XVI)

by hydrolysis, preferably under alkaline conditions, to remove the lower alkanoyl group Y'. The compound of formula XVI may be recovered as the free base or as an acid addition salt.

The reaction of the primary amine XVI with the compound of formula XVII may be carried out at elevated temperature in the presence of a suitable acidic solvent for example phenol or dilute hydrochloric acid. The reaction products may be recovered from the reaction mixtures by standard isolation procedures. In certain cases it is expedient to incorporate a protecting group for amino in the compound of formula XVI to reduce or preclude undesired reaction of the compounds of formula XVII with a primary or secondary amino function in the group R. In such cases the protecting group is removed after the reaction with the compound of formula XVII.

The compounds of formula I may be isolated in free base form or as an acid addition salt. Acid addition salts may be converted into the free base in conventional manner. The free base forms may be converted into acid addition salts in conventional manner, for instance, by adding ethereal hydrogen chloride to a solution of the free base where a hydrochloride salt is desired.

The sulphonylating agents used for reaction with a compound of formula RH can be prepared in known manner from the corresponding sulphonic acid.

The sulphonic acid may be prepared by reacting an aminobenzene -sulphonic acid of the formula:

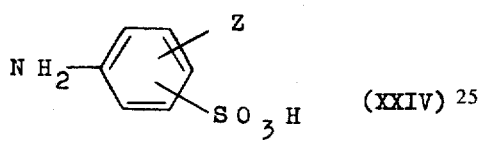

(XXIV)

where Z is as defined in connection with formula IV with a compound of formula XVII

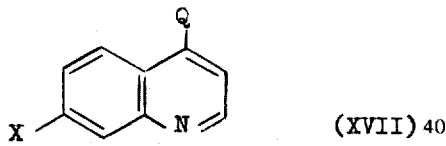

(XVII)

where X is a halogen atom or a trifluoromethyl group and Q is a group or atom replaceable by nucleophilic attack by the compound of formula XXIV. Q is for example, an iodine, bromine or chlorine atom. The secondary amine reaction product may be isolated as such or in the form of one of its salts. It may be purified salt formation and liberating the acid from the salt. The sulphonic acid or its salt may be converted into sulphonylating derivatives of the acid in known manner. For example the sulphonyl chloride of formula XV may be formed by reacting the corresponding sulphonic acid with thionyl chloride in the presence of dimethylformamide as catalyst.

Some of the compounds of formula I may also be prepared by another method using the amide of the general formula XXV

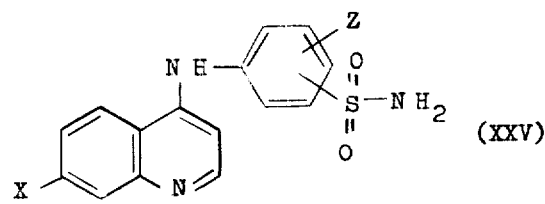

(XXV)

where X is as defined above and Z is as defined in respect of formula IV. The amide can be prepared by reaction of the sulphonyl chloride of formula XV with ammonium hydroxide solution and isolated from the reaction mixture. The invention also provides a process for the preparation of a compound having general formula I wherein R is a group of formula II or IIIa and their acid addition salts. The compounds wherein R is a group of formula II and $R_3$ is a hydrogen atom and wherein R is a group of formula IIIa whilst $R_1$ is a hydrogen atom can be obtained by alkylation of the amide of formula XXV in aqueous or alcoholic alkaline solution. By means of this alkylation the group $-A-NR_1R_2$ or the group

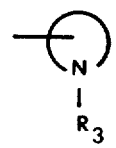

is introduced. The alkylating agent used is preferably the halide of formula:

$$\text{Hal-A-NR}_1\text{R}_2 \qquad (XXVI)$$

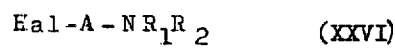 (XXVII)

where Hal stands for a halogen atom preferably chlorine, bromine or iodine. Alternatively the corresponding sulphonates or organosulphonates may be used as alkylating agents.

The compounds of formula I where R has formula II and $R_3$ is an alkyl group, an aralkyl group or an alkyl group substituted by a heterocyclic group may be prepared by two successive alkylations of the amide of formula XXV, each carried out in aqueous or alcoholic alkaline solution. In this case the alkylation carried out to introduce the group $R_3$ is preferably the second of the two reactions. Thus, for example, compounds of formula I where R is a group of formula II may be prepared by the reaction sequence

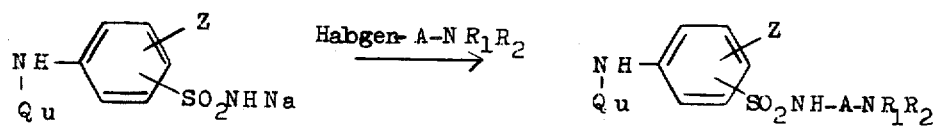

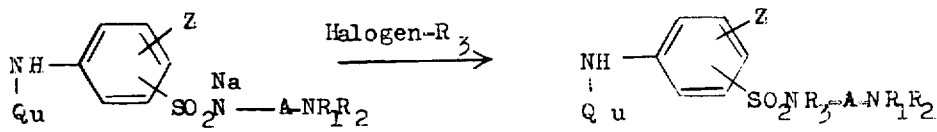

where Qu is the 7-(halo or trifluoromethyl)-4-quinolyl residue. Similarly the compounds of formula I where R is a group of formula IIIa and R₁ is an alkyl or aralkyl group may be prepared by two successive alkylations of the amide of formula XXV in aqueous or alcoholic alkaline solution. One such alkylation introduces the group

whilst the other introduces the group R₁. The reaction medium used for the alkylation of the amide of formula XXV may be an aqueous solution of sodium or potassium hydroxide. Alternatively the alkaline solution may be prepared from a lower alkanol, for example ethanol. The products of the alkylation steps may be recovered as such or as the acid addition salts in accordance with conventional isolation procedures.

The compounds of formula I and their pharmaceutically acceptable acid addition salts are indicated for pharmacological usage and, in some cases, for use as intermediates for the preparation of other compounds of formula I. For instance, the compounds of formula I demonstrate anti-hypertensive activity and, in some cases, also demonstrate at least one of the following activities: anti-malarial activity, anti-inflammatory activity, anti-trichomonal activity and inhibition of blood platelet aggregation. For example, in addition to their anti-hypertensive activity, 4-(7-chloro-4-quinolyamino)-N-(1-ethyl-3-piperidyl)benzenesulphonamide shows anti-inflammatory activity, anti-trichomonal activity and inhibition of blood platelet aggregation and 4-dimethylamino-1-[4-(7-chloro-4-quinolyamino)-benzenesulphonyl]-piperdine shows anti-malarial and anti-trichomonal activity. The compounds are evaluated for their activity by testing in standard procedures. Some of the compounds of the invention may also be used as intermediates for the preparation of other compounds conforming with formula I. For example, compounds containing a phthalimido group as —NR₁R₂ in formula II or IIb may be subjected to cleavage using hydrazizne to form a corresponding compound containing an amino group (—NH₂) as —NR₁R₂ and compounds containing an amino group may be alkylated to form a corresponding compound with an alkyl-substituted amino groups.

The invention also includes pharmaceutical compositions containing as active ingredients a compound of formula (I) or a pharmaceutically acceptable acid addition salt thereof, which may be micronised if desired. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavoring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The invention is illustrated by the following Examples:

EXAMPLE 1

4-(7-Chloro-4-quinolylamino)-N-(1-ethyl-3-piperidyl)-benzenesulphonamide.

a. 39.61 Grams of 4,7-dichloroquinoline and 34.64 grams of p-aminobenzenesulphonic acid in 130 grams of phenol were heated to 180°C for 2 hours. The solution obtained on cooling was poured into two liters of isopropyl alcohol and the mixture stirred for ½ hour. The solid formed was filtered, washed with warm isopropyl alcohol and dried to give 24.6 grams of 4-(7-chloro-4-quinolylamino benzenesulphonic acid. Melting point >300°C.

Analysis: Found 54.1% C, 3.6% H, 8.1% N. $C_{15}H_{11}ClN_2O_3S$ requires 53.8% C, 3.3% H, 8.4% N.

b. 16.45 Grams of 4-(7-chloro-4-quinolylamino)benzenesulphonic acid were heated under reflux for two hours with 200 milliliters of thionyl chloride and two drops of dimethylformamide to generate the sulphonyl chloride hydrochloride. After the excess thionyl chloride had been removed on the rotary evaporator, 7.8 grams of the pungent smelling, yellow solid were added in portions, to a stirred mixture of 2.6 grams of 3-amino-1-ethylpiperidine and 21.5 grams of sodium carbonate in 150 milliliters of water and 150 milliliters of chloroform.

After stirring overnight at room temperature, the chloroform layer was separated, washed with water and dried over magnesium sulphate, filtered and evaporated. The residue was dissolved in hot ethanol and ethereal hydrogen chloride added. The precipitated solid was filtered and washed with isopropyl alcohol, and dried to give 6.3 grams of the title compound as the dihydrochloride monohydrate. Melting point = 210°–212°C.

Analysis found: 49.3% C, 5.2% H, 10.0% N. $C_{22}H_{29}Cl_3N_4O_3S$ requires 49.3% C, 5.45% H, 10.4% N.

EXAMPLE 2

4-Dimethylamino-1-[4-(7-chloro-4-quinolylamino)-benzenesulphonyl]piperidine.

11.3 Grams of 4-(7-chloro-4-quinolylamino)-benzenesulphonyl chloride hydrochloride [prepared as in Example 1(b)] were added in portions to a stirred mixture of 5.83 grams of 4-dimethylamino-piperidine dihydrochloride and 32 grams of sodium carbonate in 100 milliliters of water and 75 milliliters of chloroform. After stirring overnight at room temperature the mixture was filtered, the resultant solid washed with water, dried and recrystallised from ethanol/water to give 6.28 grams of the title compound. Melting point 230°–231°C.

Analysis found: 59.1% C; 5.70% H; 12.2% N. $C_{22}H_{25}ClN_4O_2S$ requires 59.4% C; 5.66% H; 12.6% N.

EXAMPLE 3

4-(7-Chloro-4-quinolylamino)-N-(1-n-butyl-4-piperidyl)-benzene sulphonamide.

7.8 Grams of 4-(7-chloro-4-quinolylamino)-benzenesulphonyl chloride hydrochloride [prepared as in Example 1(b)] were added in portions to a stirred mixture of 3.13 grams of 4-amino-1-n-butyl piperidine and 21.2 grams of sodium carbonate in 50 milliliters of water and 50 milliliters of chloroform. After stirring overnight at room temperature, the chloroform layer was separated, washed with water, dried and evaporated to give a brown solid which was triturated with ether to give 5.0 grams of the title compound as the hemihydrate. Melting point 190°–191°C.

Analysis: Found 59.7% C; 6.35% H; 11.4% N. $C_{24}H_{29}ClN_4O_2S \cdot \frac{1}{2}H_2O$ requires 59.8% C; 6.27% H; 11.6% N.

EXAMPLE 4

4-Acetamido-N-(1-n-butyl-4-piperidyl)-benzenesulphonamide.

a. 7.0 Grams of N-acetylsulphanilyl chloride were added in portions to a stirred, ice cooled, mixture of 4.7 grams of 4-amino-1-n-butyl piperidine and 6.3 grams of sodium bicarbonate in 75 milliliters of water and 35 milliliters of chloroform. After stirring overnight at room temperature the mixture was filtered, washed with water, and dried to give 4.2 grams of the title compound. Melting Point 174°–175°C.

Analysis: Found 57.9% C; 7.9% H; 12.05% N; $C_{17}H_{27}N_3O_3S$ requires 57.8% C; 7.70% H; 11.9% N.

EXAMPLE 5

4-Amino-N-(1-n-butyl-4-piperidyl)-benzenesulphonamide.

8.1 Grams of 4-acetamido-N-(1-butyl-4-piperidyl)-benzensulphonamide were refluxed in 40 milliliters of 2N sodium hydroxide for ninety minutes. On cooling 2N hydrochloric acid was added to precipitate 6.7 grams of the title compound as the hemihydrate. Melting point 137°–138°C.

Analysis: Found 56.1% C; 7.92% H; 12.9% N. $C_{15}H_{25}N_3O_2S \cdot \frac{1}{2}H_2O$ requires: 56.2% C; 8.18% H; 13.1% N.

4-Amino-N-(1-n-butyl-4-piperidyl)benzenesulphonamide is useful for the preparation of 4-(7-chloro-4-quinolylamino)-N-1-4-piperidyl)-benzenesulphonamide by reaction with 4,7-dichloroquinoline in dilute hydrochloric acid.

EXAMPLE 6

4-(7-Chloro-4-quinolyamino)-N-(1-benzyl-4-piperidyl)-benzenesulphonamide.

9.7 Grams of 4-(7-chloro-4-quinolylamino)-benzenesulphonyl chloride hydrochloride [prepared as in Example 1(b)] were added in portions to 4.76 grams of 4-amino-1-benzylpiperidine and 26.5 grams of sodium carbonate in 60 milliliters of water and 60 milliliters of chloroform. After stirring overnight at room temperature, the chloroform layer was separated, washed with water, dried and evaporated to give a gum which was dissolved in hot benzene and n-hexane added to precipitate 2.0 grams of the title compound as the hemihydrate. Melting point: 90°–93°C.

Analysis: Found 62.8% C; 5.70% H; 10.7% N. $C_{27}H_{27}ClN_4O_2S \cdot \frac{1}{2}H_2O$ requires 62.8% C; 5.47% H; 10.8% N.

EXAMPLE 7

4-(7-Chloro-4-quinolylamino)-N-(1-cyclohexyl-4-piperidyl)-benzene-sulphonamide.

7.8 Grams of 4-(7-Chloro-4-quinolylamino)-benzenesulphonyl chloride hydrochloride [prepared as in Example 1(b)] were added in portions to a stirred ice-cooled mixture of 3.63 grams of 4-amino-1-cyclohexylpiperidine and 21.2 grams of sodium carbonate in 60 milliliters of water and 50 milliliters of chloroform. After stirring overnight at room temperature the chloroform layer was separated, washed with water, dried and evaporated to give a brown solid. This was triturated with hexane, the resultant solid dissolved in chloroform and diiso-propyl ether added to precipitate a solid which was triturated with hexane to give 1.9 grams of the title compound as the hemihydrate. Melting point 192°–193°C.

Analysis: Found 61.7% C; 6.42% H; 10.6% N. $C_{26}H_{31}ClN_4O_2S.\tfrac{1}{2}H_2O$ requires 61.5% C; 6.35% H; 11.0% N.

EXAMPLE 8

3-(4-Acetamidobenzenesulphonamido)-1-ethylpiperidene.

7.86 Grams of 3-amino-1-ethyl piperidine and 12.6 grams of sodium bicarbonate in 150 milliliters of chloroform and 150 milliliters of water were stirred at 10°C. 13.01 grams of 4-acetamidobenzenesulphonyl chloride was added portionwise while the temperature was maintained at 10°C. The mixture was stirred at room temperature overnight, the solid formed was filtered, washed with water and dried under vacuum to give the title compound as a hydrate, melting point 65°–68°C.

Analysis calculated: C, 52.45%; H, 7.3%; N, 12.2%; Found: C, 52.8%; H, 7.1%; N, 12.1%.

EXAMPLE 9

3-(4-Aminobenzenesulphonamido)-1-ethylpiperidine.

A solution of 4.06 grams of 3-(3-acetamidobenzenesulphonamido)-1-ethylpiperidine in 200 milliliters of 2N sodium hydroxide solution was refluxed for 1 hour. The mixture was cooled and acidified with 2N hydrochloric acid to pH 6.5. The solid formed was filtered, dried under vacuum and recrystallised from 95% ethanol to give the title compound, melting point, 163°–4°C.

Analysis calculated, C, 55.1%; H, 7.5%; N, 14.8%. Found: C, 54.8%; H, 7.3%; N, 14.7%.

EXAMPLE 10

4-(7-Chloro-4-quinolylamino)-N-(1-ethyl-3-piperidyl)-benzenesulphonamide.

A solution of 2.83 grams of 3-(4-aminobenzenesulphonamido)-1-ethylpiperidine and 1.98 grams of 4,7-dichloroquinoline in 20 milliliters of 2N hydrochloric acid was refluxed for 1 hour. The cooled solution was basified with ammonia solution to pH 8 and extracted into chloroform (3 × 25 milliliters). The extracts were dried over magnesium sulphate and evaporated. The gummy residue was dissolved in isopropyl alcohol and the product precipitated with ethereal hydrogen chloride to give the title compound as the dihydrochloride.

The product has identical melting point and infra-red spectrum to the product obtained in Example 1(b)

EXAMPLE 11

4-Benzamido-1-(4-[7-chloro-4-quinolylamino]benzenesulphonylpiperidine.

4.08 Grams of 4-benzamidopiperidine and 21.5 grams of sodium carbonate in 100 milliliters of chloroform and 100 milliliters of water were stirred at 10°–15°C. 7.79 grams of 4-(7-chloro-4-quinolylamino)benzenesulphonyl chloride hydrochloride was added portionwise and the temperature was maintained at 10°–15°C during the addition. The mixture was stirred at room temperature overnight and the solid formed was filtered, washed with water, dried under vacuum and recrystallised from 1:10 mixture of N,N-dimethylformamide and ethanol to give the title compound as the ethanolate, melting point 266°–267°C.

Analysis calculated, C, 61.4%; H, 5.5%; N, 9.9%. Found: C, 61.1%; H, 5.5%; N, 9.8%.

EXAMPLE 12

4-(7-Chloro-4-quinolylamino)-N-(1-methyl-4-piperidyl)benzenesulphonamide.

7.8 Grams of 4-(7-chloro-4-quinolyamino)benzenesulphonyl chloride hydrochloride [prepared as in Example 1(b)] were added in portions to a stirred mixture of 2.3 grams of 4-amino-1-methylpiperidine and 21.0 grams of sodium carbonate in 60 milliliters of chloroform and 90 milliliters of water. After stirring overnight at room temperature, the chloroform layer was separated, dried and evaporated. The residue was triturated with hexane to give 8.4 grams of the title compound as its monohydrate. Melting point, 184°–185°C.

Analysis: Found, 56.1% C; 5.33% H; 12.1% N. $C_{21}H_{25}ClN_4O_3S$ requires: 56.2% C; 5.61% H, 12.5% N.

EXAMPLE 13

4-(7-chloro-4-quinolylamino)-N-(2-diethylaminoethyl)-benzenesulphonamide 7.8 Grams of 4-(7-chloro-4-quinolylamino)benzenesulphonyl chloride hydrochloride (prepared as in Example I(b)) were added in portions to a stirred mixture of 2.3 grams of N,N-dimethylethylenediamine and 21.0 grams of sodium carbonate in 60 milliliters of chloroform and 90 milliliters of water. After stirring overnight at room temperature, the chloroform layer was separated, dried and evaporated. The resulting oil was triturated with hexane to give a solid which was recrystallised from benzene to give 3.8 grams of the title compound. Melting point, 161°–162°C.

Analysis: Found, 57.8% C; 5.82% H; 12.9% N, $C_{21}H_{25}ClN_4O_2S$ requires 58.2% C; 5.82% H; 12.9% N.

EXAMPLE 14

3-(7-chloro-4-quinolylamino)-N-(1-ethyl-3-piperidyl)-benzenesulphonamide.

a. 19.8 Grams of 4,7-dichloroquinoline were added to a solution of 19.5 grams of sodium metanilate in 400 milliliters of water and the solution was made acid by the addition of 20 milliliters of concentrated hydrochloric acid. The solution was refluxed for 20 minutes when a solid precipitated. On cooling the solid was collected and dried to give 29.5 grams of 3-(7-chloro-4-quinolylamino)-benzenesulphonic acid. Melting point > 300°C.

b. 3-(7-Chloro-4-quinolylamino)benzenesulphonic acid was converted to the corresponding sulphonylchloride hydrochloride and reacted with 3-amino-1-ethylpiperidine in a similar manner to that described in Example 1 (b) to give the title compound.

EXAMPLE 15

2-Chloro-4-(7-chloro-4-quinolylamino)-N-(1-n-butyl-4-piperidyl)benzene-sulphonamide a. A mixture of 31.5 grams of 3-chloronitrobenzene, 450 milliliters of 5N-sodium sulphite solution and 500 milliliters of 2N sodium hydroxide solution was refluxed with stirring for 90 minutes, acidified with concentrated hydrochloric acid, and refluxed for 1 hour. On cooling and diluting with water a solid crystallised out which was filtered and washed with water to give 9.9 grams of 2-chlorosulphanilic acid.

b. 9.9 Grams of 2-chloro sulphanilic acid and 9.4 grams of 4,7-dichloroquinoline were suspended in 200 milliliters of water and concentrated hydrochloric acid added until the solution was just acid. The mixture was refluxed for 4 hours when a solid began to precipitate. After cooling the solid was collected, washed with water and dried to give 15.8 grams of 4-(7-chloro-4-quinolylamino)-2-chlorobenzenesulphonic acid. Melting point 280°–285°C with decompostion.

c. 4-(2-Chloro-4-quinolylamino)-2-chlorobenzene sulphonic acid is converted to the corresponding sulphonylchloride hydrochloride and reacted with 4-amino-1-butylpiperidine in a similar manner to that described in Example 1(b) to give the title compound.

EXAMPLE 16

4-(7-Chloro-4-quinolyamino)-N-(1-ethyl-3-piperidyl)-2-nitrobenzene sulphonamide.

4-(7-Chloro-4-quinolylamino)-2-nitrobenzenesulphonic acid is converted to the corresponding sulphonyl chloride hydrochloride and reacted with 3-amino-1-ethyl piperidine in a similar manner to that described in Example 1(b) to give the title compound.

EXAMPLE 17

4-(7-Chloro-4-quinolylamino)-4-(1-ethyl-3-piperidyl)-3-methoxybenzene sulphonamide.

4-(7-chloro-4-quinolyamino)-3-methoxybenzene sulphonic acid is converted to the corresponding sulphonylchloride hydrochloride and reacted with 3-amino-1-ethyl-piperidine in a similar manner to that described in Example 1(b) to give the title compound.

EXAMPLE 18

4-(7-Bromo-4-quinolylamino)-N-(1-ethyl-3-piperidyl)-benzenesulphonamide.

a. 7-Bromo-4-chloroquinoline and p-aminobenzenesulphonic acid are reacted in a similar manner to that described in Example 14(a) to give 4-(7-bromo-4-quinolylamino)-benzenesulphonic acid.

b. 4-(7-Bromo-4-quinolylamino)benzenesulphonic acid is converted to the corresponding sulphonyl chloride hydrochloride and reacted with 3-amino--ethylpiperidine in a similar manner to that described in Example 1(b) to give the title compound.

What is claimed is:

1. A compound selected from those of the formula

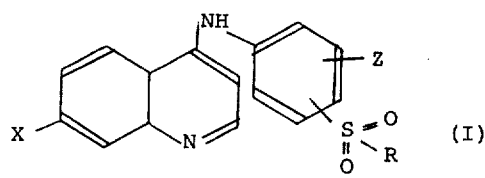

and their pharmaceutically acceptable acid addition salts, where i. x is selected from chlorine and bromine;
ii. Z is a member of the group consisting of hydrogen, lower alkoxy, nitro and chlorine;
iii. R is a member of the group consisting of

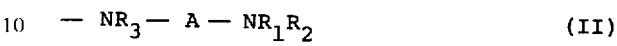

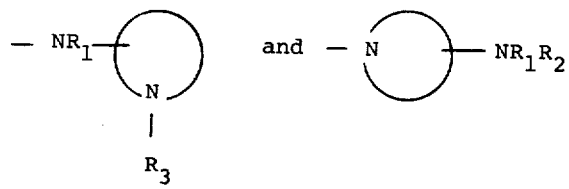

wherein
a. in formula II, A represents a chain of 1 to 5 methylene groups;
b. in formulae IIIa and IIIb the ring denotes a piperidine or pyrrolidine ring;
c. $R_1$ is a member of the group consisting of hydrogen and lower alkyl;
d. $R_2$ represents a member of the group consisting of lower alkyl and benzoyl; and
e. $R_3$ represents a member of the group consisting of hydrogen, cycloalkyl of 5 to 7 carbon atoms, lower alkyl and benzyl.

2. A compound as defined in claim 1, which is 4-(7-chloro-4-quinolylamino)-N-(1-ethyl-3-piperidyl)-benzensulphonamide or a pharmaceutically acceptable acid addition salt thereof.

3. A compound as defined in claim 1, which is 4-dimethylamino-1-[4-(7-chloro-4-quinolylamino)-benzenesulphonyl]piperidine or a pharmaceutically acceptable acid addition salt thereof.

4. A compound as defined in claim 1, which is 4-(7-chloro-4-quinolylamino)-N-(1-n-butyl-4-piperidyl)-benzensulphonamide or a pharmaceutically acceptable acid addition salt thereof.

5. A compound as defined in claim 1, which is 4-(7-chloro-4-quinolyamino)-N-(1-benzyl-4-piperidyl)benzene sulphonamide or a pharmaceutically acceptable acid addition salt thereof.

6. A compound as defined in claim 1, which is 4-(7-chloro-4-quinolylamino)-N-(1-cyclohexyl-4-piperidyl) benzenesulphonamide or a pharmaceutically acceptable acid addition salt thereof.

7. A compound as defined in claim 1, which is 4-benzamido-1-(4-[7-chloro-4-quinolylamino]benzenesulphonyl-piperidine or a pharmaceutically acceptable acid addition salt thereof.

8. A compound as defined in claim 1, which is 4-(7-chloro-4-quinolyamino)-N-(1-methyl-4-piperidyl)-benzensulphonamide or a pharmaceutically acceptable acid addition salt thereof.

9. A compound as defined in claim 1, which is 4-(7-chloro-4-quinolylamino)-N-(2-diethylaminoethyl)-benzenesulphonamide or a pharmaceutically acceptable acid addition salt thereof.

* * * * *